United States Patent [19]

Lamadrid

[11] 4,087,185
[45] May 2, 1978

[54] BLOOD LEAK DETECTOR

[75] Inventor: Rene G. Lamadrid, Silver Spring, Md.

[73] Assignee: Baxter Travenol Laboratories, Inc., Deerfield, Ill.

[21] Appl. No.: 588,513

[22] Filed: Jun. 19, 1975

[51] Int. Cl.² ............................................ G01N 21/26
[52] U.S. Cl. ...................................... 356/201; 356/181
[58] Field of Search ........... 210/321 R, 321 A, 321 B; 250/564, 565, 573–576; 356/181, 201, 208, 207, 244, 246

[56] References Cited

U.S. PATENT DOCUMENTS

| 3,480,784 | 11/1969 | Pierce | 356/246 UX |
| 3,560,099 | 2/1971 | Boe et al. | 356/246 |
| 3,819,278 | 6/1974 | Muller | 356/181 X |
| 3,832,067 | 8/1974 | Kopf et al. | 356/181 |

Primary Examiner—F. L. Evans
Attorney, Agent, or Firm—Gerald S. Geren; Paul C. Flattery

[57] ABSTRACT

A detector of blood in dialyzing solution, which operates by measuring the optical density of the dialyzing solution, is prevented from improper indication arising from the presence of bubbles in the dialyzing solution, by shaping the fluid passages to channel the bubbles away from the optical sensing path.

5 Claims, 3 Drawing Figures

BLOOD LEAK DETECTOR

SUMMARY

In kidney dialysis machines it is necessary to monitor dialysis fluid for the presence of blood, since a patient could be seriously injured by an unnoticed blood leak. In the past, transmission densitometers have been used to monitor the normally nearly transparent dialysis fluid for the abnormal presence of opaque blood. However, the prior art blood leak detectors have an unpredictable tendency to drift from their initial setting, and to indicate, at the end of a run, that the dialysis fluid is more transparent than it actually is. Thus a blood leak could be obscured by the drift of the instrument.

The invention is based on the discovery that such drift is caused by an unpredictable irregular accumulation of bubbles on the walls of the guard situated around the optical sensing path in the instrument. These bubbles, out of the direct transmission path between the light source and photocells, nevertheless act to reflect additional light from the light source to the photocell.

In the improved blood detector described herein, the shape of the guard is changed, so as to channel the bubbles away from the area in which they could affect the photocell illumination.

DETAILED DESCRIPTION OF INVENTION

Figure 1:
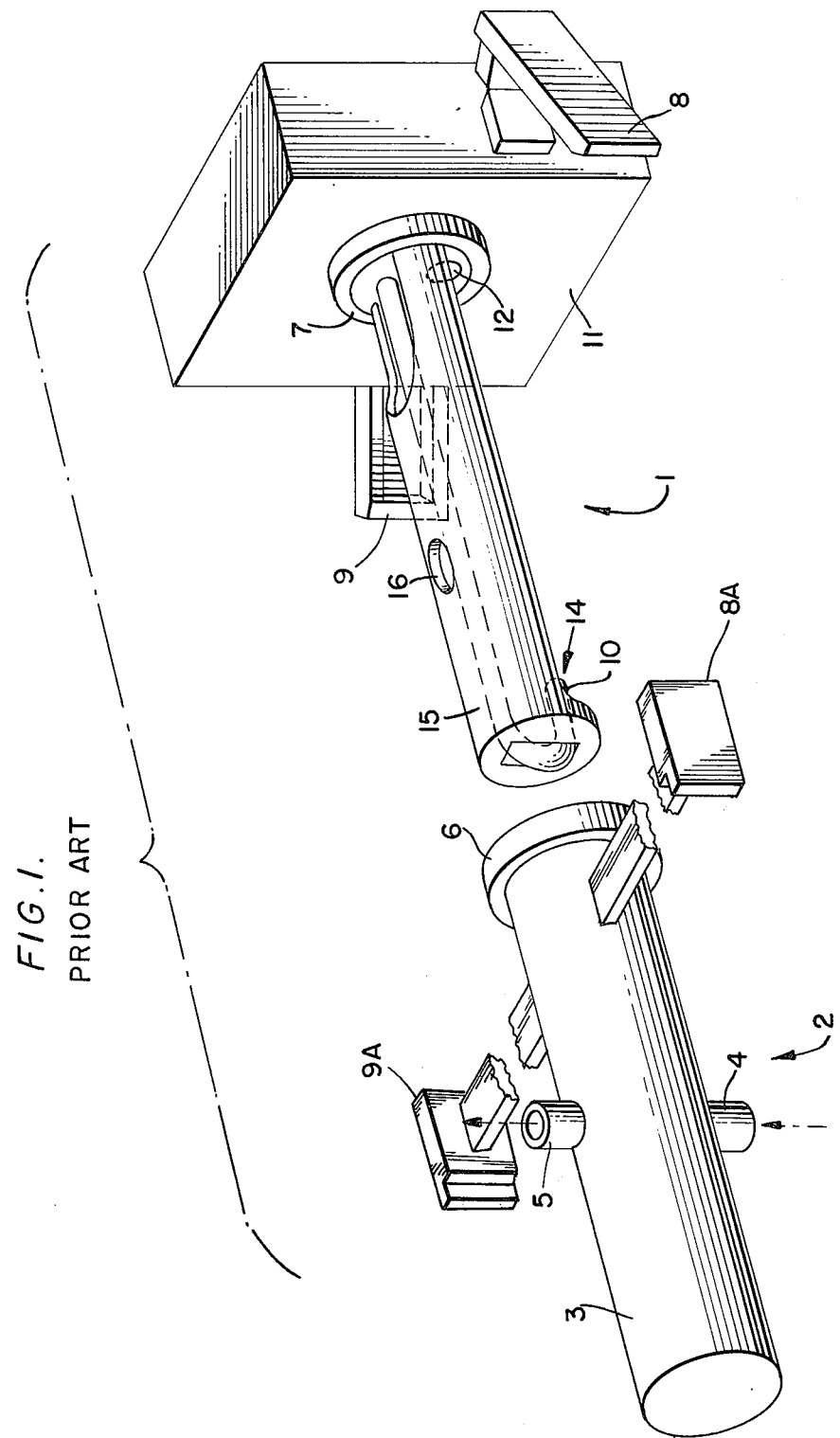
FIG. 1 shows an exploded perspective view of the prior art blood leak detector.

The exploded view of FIG. 1 shows the prior art blood pump, with the sensing probe 1 disassembled from the sensing chamber 2, as it frequently is for cleaning or other servicing.

The sensing chamber 2 is generally fixed to other parts of the equipment, since it includes base connections which are relatively difficult to disconnect, while the sensing probe 1 is generally made moveable, since it includes relatively flexible electric cables, which are readily unplugged.

The sensing chamber includes a casing 3, an inlet connection 4 for the dialyzing fluid, and an outlet connection 5. Dialyzing fluid occasionally includes bubbles, so the prior art upward flow did prevent the sensing casing 3 from becoming charged with a mass of bubbles.

The sensing chamber is also provided, at its open end, with a sealing flange 6, which is clamped against gasket means 7 by means of two toggle clamps 8 and 9 whenever the blood leak detector is assembled and in use. The connection between flange 6 and gasket 7 is then leak-tight.

The two toggle clamps 8 and 9 engage with catches 8A and 9A respectively, which are fixed to casing 3. In order to avoid confusion, the catches 8A and 9A are shown broken away from the casing 3, as in an exploded view.

The sensing probe 1 contains a light pipe 10 which has a 180° bend in it and which conducts light from a lamp (not shown) located within housing 11 towards the left end of the sensing probe and thereat provides a bright light spot at the end 14 of the light pipe. The bright light spot illuminates the window 12 of a photosensitive detector 12.

The light pipe 10 is rather fragile, and needs protection when the blood leak detector is disassembled. Accordingly, a guard 15 is provided. The guard 15 has a hole 16 in its upper side to permit the ready exit of dialyzing fluid to the outlet connection 5.

It will be realized that, in use, when the sensing probe 1 is assembled in the sensing chamber 2, the bright spot of light at the end 14 of the light pipe will illuminate the photosensitive detector 12 only through the ambient dialyzing fluid in chamber 3. That fluid may or may not contain blood, and increasing amounts of blood content should result in lesser illumination.

However, it has been found that during operation of the unit, the reading would drift in the direction indicating that the dialysis fluid was becoming more transparent.

Recently, applicant discovered that this was caused, not by faulty electronics in housing 11, but by the accumulation of bubbles within the guard 15.

The presence of even one bubble inside the guard 15 can increase the amount of light which reaches the window of the photosensitive detector 12, because the bubble, which may be far from the light path, can pick up stray light from the bright spot on the end 14 of light pipe 10 and redirect such stray light, (which normally would be lost elsewhere), to the window of the photosensitive detector 12.

These bubbles could be eliminated if the guard 15 were removed, but then bubbles would produce the same problem all over again by accumulating within the casing 3.

Figure 2:
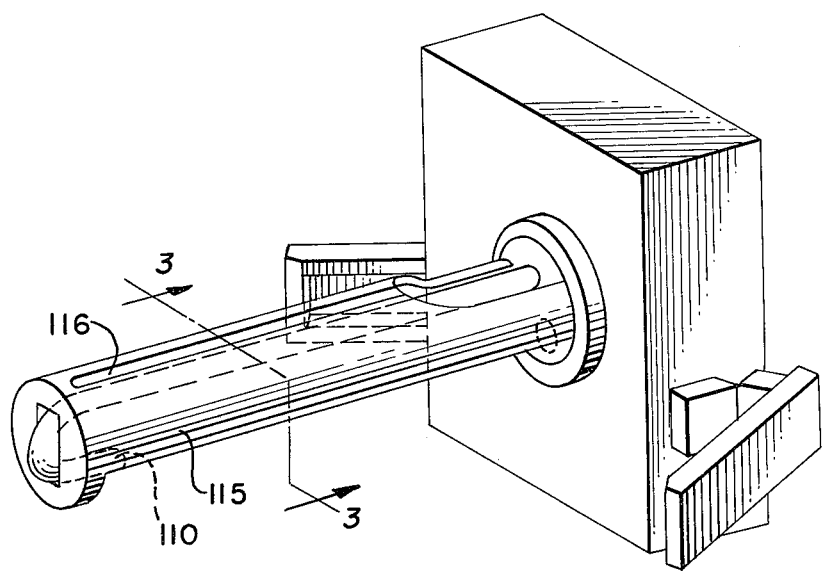
FIG. 2 shows a perspective view, corresponding to the showing of FIG. 1, of a portion of the blood leak detector in accordance with the invention.
Figure 3:
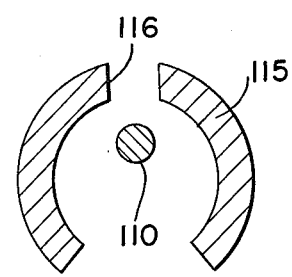
FIG. 3 shows a cross section of the portion of the apparatus shown in FIG. 2, taken along the section lines 3—3.

Applicant has discovered that the bubble problem is solved if the body of the guard 15, instead of having a round hole 16 in its upper side, has instead a longitudinal slot 116 along the entire upper length of the body of the guard 115, as shown in FIGS. 2 and 3. In FIGS. 2 and 3, similar parts have the numbers which differ by one hundred.

Referring more particularly to FIG. 3, it is seen that the slot 116 has vertical surfaces, and that all other portions of the guard are slanted far from the horizontal. Thus, bubbles will have little tendency to stick to a nearly horizontal "overhead" surface.

The width of slot 116 should be adjusted so that any bubble which is large enough to bridge the gap between the two sides of the slot also has enough buoyancy in the dialysis fluid to float the bubble through the slot, despite the bridging. A width of 0.6 centimeters has proved satisfactory. However, the slot should not be made any larger than necessary, because the guard 115 acts as a light barrier, which shields the photocell from the irradiating effects of bubbles which are outside and above guard 115 and inside the casing 3.

It is noted that bubbles do not appear to be trapped on the light pipe 110. This is probably due to the fact that the light pipe 110 is of rather small diameter and is situated in a more exposed position in the dialysis fluid. That is, stagnation of the dialysis fluid flow is more likely closely adjacent to larger surfaces, such as those of guard 115 or casing 3.

The use of the new shape of guard has solved the problem of drift of the reading. Such drift, occasioned by accumulation of bubbles, is in the opposite direction as is the indication for the presence of blood. Hence, such drift is not fail-safe, but is fail-danger.

The invention, while described with reference to one embodiment, obviously can be carried out in various ways, without departure from the teachings of this disclosure.

What is claimed as my invention is:

1. In a detector, comprising
a hydraulic circuit for circulating a fluid, which is to be optically sensed, through a chamber
an optical probe for testing the optical transmission of said fluid in said chamber
said optical probe being releasably and sealingly insertable into said chamber for optical coupling to said fluid,
a guard means around said optical probe for mechanically protecting said probe against impact or force damage when the probe is being handled and to optically protect said probe against stray light when said probe is in use, the improvement wherein said guard means defines a body having an upper portion and a lower portion, said lower portion having a first slot means for allowing entry of said fluid, said upper portion defining a second slot means allowing exiting of said fluid, said second slot means further providing means for free escape of bubbles which may be contained in said fluid as it passes through said first slot means and said second slot means, and said guard means defining internal surfaces at an angle to the horizontal to facilitate movement of bubbles toward said first slot means.

2. A detector, as in claim 1, in which the fluid is dialysis fluid, which may fortuitously contain blood, and in which the measured optical transmission is a measure of the presence of blood in the dialysis fluid.

3. The detector according to claim 1 wherein said first slot means extends substantially the entire length of said guard means parallel to the axis thereof.

4. In a detector, comprising
a hydraulic circuit for circulating a fluid, which is to be optically sensed, through a chamber,
an elongated optical probe for testing the optical transmission of said fluid in said chamber,
said optical probe being releasably and sealingly insertable into said chamber for optical coupling to said fluid,
a substantially cylindrical guard means concentrically surrounding said optical probe such that the longitudinal axis of the guard means coincides with that of the probe for mechanically protecting said probe against impact or force damage when the probe is being handled and to optically protect said probe against stray light when said probe is in use, and
the improvement wherein said guard means defines a body having an upper portion and a lower portion, said lower portion having a first slot means extending substantially the entire length of said guard means parallel to the axis thereof for allowing entry of said fluid, said upper portion defining a second slot means allowing exiting of said fluid, said second slot means further providing means for free escape of bubbles which may be contained in said fluid as it passes through said first slot means and said second slot means, said guard means defining internal surfaces at an angle to the horizontal to facilitate movement of bubbles toward said first slot means, and the first and second slot means being parallel to the longitudinal guard means and probe axes.

5. The detector according to claim 4 further defining a casing to sealingly engage said probe and guard means, said casing having a fluid inlet and fluid outlet for allowing entry and exit, respectively, of the fluid to be sensed.

* * * * *